(12) United States Patent
Shea et al.

(10) Patent No.: US 9,889,013 B2
(45) Date of Patent: Feb. 13, 2018

(54) VARIABLE ANGLE BLADE AUGMENT

(71) Applicant: Smith & Nephew, Inc., Memphis, TN (US)

(72) Inventors: Jeffrey Joel Shea, Memphis, TN (US); Richard Douglas Lambert, Collierville, TN (US); Michael Scott Bennett, Southaven, MS (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 15/026,778

(22) PCT Filed: Nov. 25, 2015

(86) PCT No.: PCT/US2015/062649
§ 371 (c)(1),
(2) Date: Apr. 1, 2016

(87) PCT Pub. No.: WO2016/086119
PCT Pub. Date: Jun. 2, 2016

(65) Prior Publication Data
US 2016/0317308 A1 Nov. 3, 2016

Related U.S. Application Data

(60) Provisional application No. 62/084,919, filed on Nov. 26, 2014.

(51) Int. Cl.
*A61F 2/32* (2006.01)
*A61F 2/30* (2006.01)
*A61F 2/34* (2006.01)

(52) U.S. Cl.
CPC ...... *A61F 2/30749* (2013.01); *A61F 2/30734* (2013.01); *A61F 2/34* (2013.01);
(Continued)

(58) Field of Classification Search
CPC ...... A61F 2/30; A61F 2/32; A61F 2/34; A61F 2/30767; A61F 2/30734; A61F 2002/30736; A61F 2002/30738
See application file for complete search history.

(56) References Cited

U.S. PATENT DOCUMENTS 5,176,711 A * 1/1993 Grimes ............. A61B 17/1666
623/22.22
5,702,457 A * 12/1997 Walch ................... A61F 2/4014
623/19.13

(Continued)

FOREIGN PATENT DOCUMENTS

DE 4133433 C1 5/1993
EP 0628294 A1 12/1994
WO 2013086235 A1 6/2013

OTHER PUBLICATIONS

International Search Report; European Patent Office; International Application No. PCT/US2015/062649; dated Feb. 17, 2016; 4 pages.

(Continued)

*Primary Examiner* — Alvin Stewart
(74) *Attorney, Agent, or Firm* — Taft Stettinius & Hollister LLP (57) ABSTRACT

A variable angle blade augment including an augment section and a separate plate or blade segment. According to some embodiments, a first connector of the blade segment and a socket capture mechanism of the augment section provide a ball and socket type joint. Additionally, the socket capture mechanism may be structured to allow for linear displacement of the first connector relative to at least one axis of the socket capture mechanism. By allowing for at least pivotal and linear relative displacement of the augment section and the blade segment, the variable angle blade augment may improve the ability to optimally position a (Continued)

buttress augment against a prosthetic acetabular shell. Moreover, the variable angle blade augment may provide the ability to utilize components of an implantable medical device after stabilizing the components to a bone structure of a patient.

20 Claims, 8 Drawing Sheets

(52) U.S. Cl.
CPC . *A61F 2/30942* (2013.01); *A61F 2002/30028* (2013.01); *A61F 2002/30364* (2013.01); *A61F 2002/30369* (2013.01); *A61F 2002/30378* (2013.01); *A61F 2002/30449* (2013.01); *A61F 2002/30507* (2013.01); *A61F 2002/30538* (2013.01); *A61F 2002/30553* (2013.01); *A61F 2002/30578* (2013.01); *A61F 2002/30583* (2013.01); *A61F 2002/30649* (2013.01); *A61F 2002/30738* (2013.01)

(56) References Cited

U.S. PATENT DOCUMENTS

| | | | | |
|---|---|---|---|---|
| 5,916,268 A * | 6/1999 | Schollner | ........... | A61B 17/1746 623/22.36 |
| 6,162,257 A * | 12/2000 | Gustilo | ................. | A61B 17/15 623/22.32 |
| 6,340,370 B1 * | 1/2002 | Willert | ..................... | A61F 2/34 623/22.21 |
| 6,454,809 B1 * | 9/2002 | Tornier | ............... | A61F 2/30724 623/22.32 |
| 6,818,019 B2 * | 11/2004 | Horber | .................. | A61F 2/4014 403/90 |
| 7,011,686 B2 * | 3/2006 | Ball | ..................... | A61F 2/4014 623/19.14 |
| 7,615,080 B2 * | 11/2009 | Ondrla | .................. | A61F 2/4014 623/19.11 |
| 7,695,473 B2 * | 4/2010 | Ralph | .................... | A61B 17/80 606/71 |
| 7,740,661 B2 * | 6/2010 | Baratz | ................... | A61F 2/3804 623/20.11 |
| 8,114,091 B2 * | 2/2012 | Ratron | .................... | A61B 17/15 606/86 R |
| 8,597,365 B2 * | 12/2013 | Meridew | .................... | A61F 2/34 623/22.32 |
| 8,663,333 B2 * | 3/2014 | Metcalfe | ................ | A61F 2/4014 623/19.11 |
| 8,828,089 B1 * | 9/2014 | Perez | ................... | A61F 2/30734 606/91 |
| 9,345,576 B2 * | 5/2016 | Shea | .................... | A61F 2/30734 |
| 9,427,320 B2 * | 8/2016 | Meridew | .................... | A61F 2/34 |
| 9,474,618 B2 * | 10/2016 | Bickley | ..................... | A61F 2/40 |
| 9,603,712 B2 * | 3/2017 | Bachmaier | ............ | A61F 2/4014 |
| 2008/0021568 A1 * | 1/2008 | Tulkis | .................. | A61F 2/30734 623/22.35 |
| 2009/0204225 A1 * | 8/2009 | Meridew | ............. | A61F 2/30734 623/22.21 |
| 2009/0326670 A1 * | 12/2009 | Keefer | ................ | A61F 2/30734 623/22.22 |
| 2011/0106258 A1 * | 5/2011 | Blackwell | ........... | A61F 2/30734 623/17.16 |
| 2013/0338786 A1 * | 12/2013 | Haidukewych | ... | A61M 5/31596 623/22.32 |
| 2014/0343686 A1 * | 11/2014 | Shea | .................... | A61F 2/30734 623/23.43 |
| 2015/0351917 A1 * | 12/2015 | Link | .................... | A61F 2/30734 623/22.11 |
| 2016/0193051 A1 * | 7/2016 | Budhabhatti | ........ | A61F 2/30734 623/19.11 |
| 2016/0262895 A1 * | 9/2016 | Shea | ................... | A61F 2/30734 |

OTHER PUBLICATIONS

Written Opinion of the International Searching Authority; European Patent Office; International Application No. PCT/US2015/062649; 6 pages.

* cited by examiner

VARIABLE ANGLE BLADE AUGMENT

CROSS REFERENCE TO RELATED APPLICATIONS

The present application is a U.S. National Phase of International PCT Application No. PCT/US2015/062649 filed Nov. 25, 2015, which claims the benefit of U.S. Provisional Patent Application No. 62/084,919 filed Nov. 26, 2014, the contents of each application hereby incorporated by reference in their entirety.

BACKGROUND

Embodiments of the present invention generally relate to the field of implantable orthopedic medical devices. More particularly, but not exclusively, embodiments of the present invention relate to implants for revision acetabular surgery.

Joints often undergo degenerative changes that necessitate replacing the joint with a prosthetic joint. For example, the hip joint may be replaced with two bearing surfaces between the femoral head and the acetabulum. The first bearing surface is often a prosthesis shell or acetabular cup having a liner that provides an inner bearing surface that receives and cooperates with art artificial femoral head in an articulating relationship to track and accommodate relative movement between the femur and acetabulum.

In at least some instances, a second or subsequent surgery may be performed to replace a prosthetic joint with another replacement prosthetic joint. Such replacement of the original prosthetic joint may be performed for a number of reasons including, for example, the need to remove diseased or degenerated bone. Further, these additional surgeries often require the replacement of the original prostheses with a larger or enhanced prosthetic joint, often referred to as a revision prosthesis. With respect to acetabular revision surgery, an acetabular prosthesis may include additional mounting elements such as, for example, augments that provide additional support and/or stability for the replacement prosthesis. These additional mounting or attachment members are often required due to bone degeneration, bone loss or bone defects in the affected area (i.e., the hip joint). Moreover, such bone deficiencies or defects often present challenges in attaining optimized and structurally sound prosthetic fixation to the host bone. Accordingly, mounting members may be provided in conjunction with a prosthesis system in order to aid the surgeon in achieving optimal fixation of the prosthetic joint, or a component of the prosthetic joint, to a bone of the patient.

Prior attempts to provide such mounting attachments (i.e., augments) with modularity have often fallen short, and instead typically provide a few discrete positions at which the mounting members may be positioned. For example, an ongoing challenge is to align implantable medical devices such as, for example, reconstructive devices, to the natural physiology of a patient. Proper alignment often may at least assist in attaining optimal wear resistance and optimal performance for many devices. Yet, patient anatomical variations present challenges in providing a medical device that may be properly aligned for each patient. For example, contemporary medical devices that address complex revision acetabular surgery may include multiple buttress augment designs that are dedicated for supporting particular sides or areas of the acetabular cup. Yet, the buttress surface of augments is typically shaped or contoured along a fixed angle or angles. Further, such fixed angles often provide an optimal match for the variations for only some patients' anatomies, and may not allow for an optimal match with other patients' anatomies.

Limitations relating to the available angles at which augment devices may be aligned, as well as augment devices having separated hand or orientation designations, among other limitations, often provide obstacles to both the installation and cost of these types of implantable medical devices. For example, medical implants that are provided in multiple directional or hand orientations may add complexity to the surgical procedure. Moreover, the time associated with at least the selection and confirmation that the correct hand side configuration of the medical device has been selected for implantation in a patient may reduce the time available to the surgeon to attain proper alignment and/or positioning of all of components of the medical device during the implantation procedure. Additionally, different hand configurations may increase the costs associated with procuring, storing, and/or otherwise having readily available an appropriate quantity of implantable devices. Moreover, the time and effort during surgery to properly match the fixed angles of buttress surfaces and the acetabular cup with the patient's particular anatomy may adversely impact the time available to the surgeon to address other aspects of the implantation procedure.

Thus, there remains a need for improved orthopedic medical devices for use in revision acetabular surgeries. The present invention addresses this need and provides other benefits and advantages in a novel and non-obvious manner.

One aspect of the present invention relates to a variable angle blade augment that may improve the ability to optimally position for a wide range of patients a buttress augment against a prosthetic acetabular shell on one end and against a host no on the other end. The ease of installation of the variable angle blade augment of the present invention may provide the surgeon with an extended amount of time to optimally position components of an implantable medical device before the construction of the variable angle blade augment is unitized through a mechanical connection, such as, for example, a mechanically tightened ball and socket joint, and/or via use of an adhesive, including, for example, bone cement. Moreover, the present invention provides the ability to optimally position adjacent prosthetic components, as well as the ability to unitize at least some components after stabilizing at least some of the components with bone screws, among other adjustable fixation devices, anchors or components. Such a construction also eliminates the need for left, right and center buttress augment designs. However, in other embodiments, the construction may be configured to facilitate a fit for either left hand or right hand configurations.

Another aspect of the present invention is directed to a variable angle blade augment that includes an augment section and a blade segment. According to some embodiments, the augment section may include a socket wall and an abutment surface. The socket wall may generally define an aperture that is adapted to provide a socket capture mechanism. The abutment surface may be adapted to abut against at least an outer surface of a component of an implantable medical device. Additionally, according to some embodiments, the blade segment may have a body segment and an extension. The body segment may have a first side, a second side, a first end, and a second end. The extension may have a first connector that is adapted for at least pivotally displacement relative to the aperture. Further, the aperture may be adapted to permit linear displacement of the first connector relative to opposing first and second end portions of the aperture.

Another aspect of the present invention is directed to a variable angle blade augment that includes an augment section and a blade portion. The augment section may include a body region that has a front portion, a rear portion, a reservoir, and an aperture. At least a portion of the front portion may be adapted to abut against at least an outer surface of a component of an implantable medical device. Additionally, the reservoir may be in fluid communication with the aperture and adapted to receive the injection of an adhesive that is configured to unitize at least the augment section with the component of the implantable medical device. The blade segment may include a body segment and an extension, with the body segment having a first side, a second side, a first end, and a second end. The extension includes a first connector, at least a portion of which is adapted to be coupled to the augment section by a mechanical connection.

Other aspects of the present invention will become apparent by consideration of the detailed description and the accompanying drawings.

BRIEF DESCRIPTION OF THE DRAWINGS

The description herein makes reference to the accompanying figures wherein like reference numerals refer to like pails throughout the several figures and views.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings. Additionally, the description herein makes reference to the accompanying figures wherein like reference numerals refer to like parts throughout the several views.

DESCRIPTION OF THE ILLUSTRATED EMBODIMENTS

Figure 1:
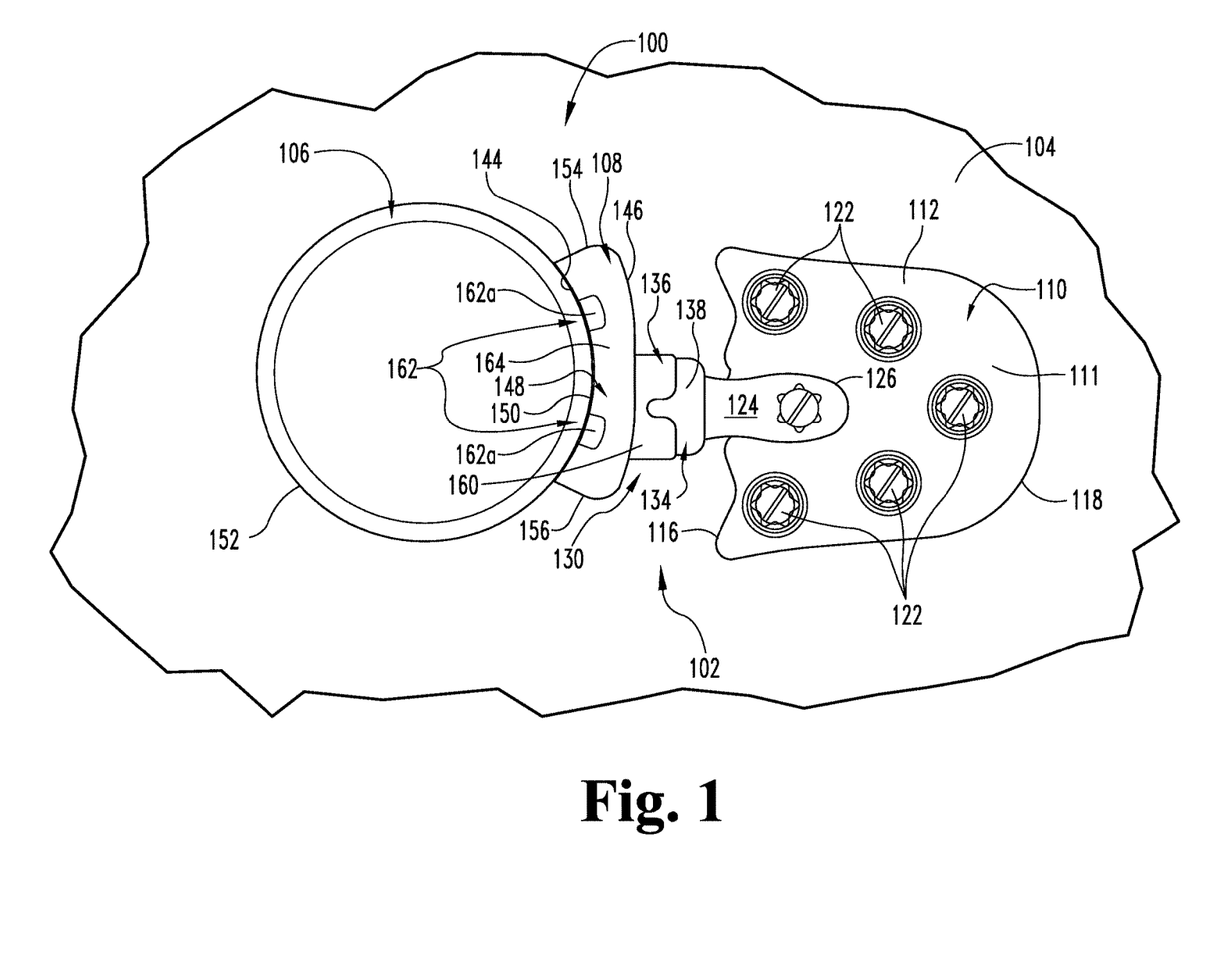
FIG. 1 illustrates a top view of an exemplary implantable medical device having a variable angle blade augment that is operably secured to a bone structure of a patient according to one embodiment.

FIG. 1 illustrates a top view of an exemplary embodiment of an implantable medical device 100 having a variable angle blade augment 102 that is operably secured to a bone structure or bone element 104 of a patient according to one form of the present invention. The exemplary implantable medical device 100 generally includes an acetabular can 106 that is supported, at least in part, by the variable angle blade augment 102. In the illustrated embodiment, the variable angle blade augment 102 includes an augment section 108 and a separate plate or blade portion 110.

Figure 2:
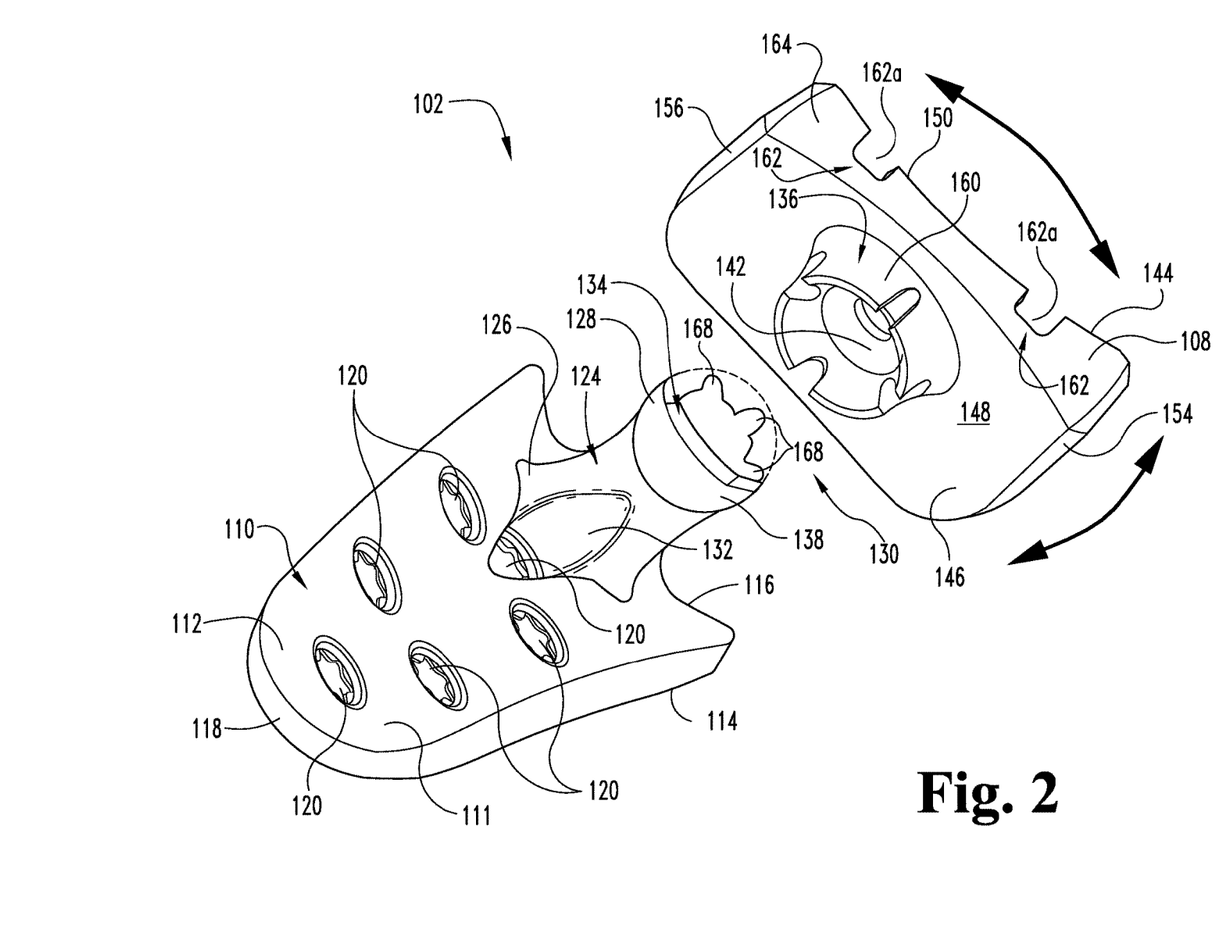
FIG. 2 illustrates an exploded side perspective view of an augment section and a separate plate or blade portion of the variable angle blade augment shown in FIG. 1.

FIG. 2. illustrates an exploded side perspective view of the variable angle blade augment 102 shown in FIG. 1, and more particularly shows a perspective view of the augment section 108 and the plate or blade portion 110. As shown, the plate or blade portion 110 may include a body segment 111 having a first side 112 and an opposite second side 114, as well as opposite first and second end portions 116, 118. As discussed below, the first end portion 116 may be adapted to provide a cement buttress that is used to secure the variable angle blade augment 102 to the acetabular cup 106 and/or the bone structure 104. Additionally, in other embodiments, the shape or contouring of the second side 114 of the body segment 111, which may be implanted adjacent to the bone structure 104 of the patient, may be manufactured or otherwise formed or contoured to match the anatomy of the patient based on pre-operative imaging or manipulation. In still other embodiments, the first side 112 of the body segment 111 may be polished so as to prevent or minimize the first side 112 from irritating or traumatizing adjacent soft tissue. Additionally, the variable angle blade augment 102 can be constructed from a variety of different materials, or combination of materials. For example, according to some embodiments, at least a portion of the variable angle blade augment 102 such as, for example, the second side 114 of the body segment, may be constructed of a porous material that can at least assist in facilitating bone in-growth into the porous material.

The body segment 111 may further include a plurality of orifices or openings 120 (FIG. 2) that generally extend through the body segment 111. The orifices 120 may each be sized and shaped to operably receive one or more mechanical fasteners 122 (FIG. 1) such as, for example, a screw, bolt, pin, and other types of suitable fasteners or anchors, that are used to secure the plate or blade portion 110 to the bone structure 104 of the patient.

The plate or blade portion 110 may also include an extension 124 that extends generally from the first end portion 116 of the plate or blade portion 110. The extension 124 may have a proximal end 126 and a distal end 128, with the proximal and 126 coupled to the body segment 111. Further, in some embodiments, the proximal end 126 may be configured to include a recess or contoured region 132 adapted to accommodate placement of at least one of the orifices 120a and/or to prevent the extension 124 from interfering with insertion and/or engagement of a fastener 122 in the orifice 120a. As discussed in further detail below, the proximal end 126 and/or the distal end 128 of the extension 124 may be adapted to allow the plate or blade portion 110 to at least pivotally, angularly and/or rotationally engage the augment section 108 via a modified socket joint 130 in a manner that also permits linear displacement of the plate or blade portion 110 relative to the augment section 108.

According to some embodiments, the distal end 128 of the extension 24 may be adapted to provide a first connector 134 for the modified socket joint 130, while the augment section 108 may be adapted to provide a mating socket capture mechanism 136. Conversely, according to other embodiments, the distal end 128 of the extension 124 may be adapted to provide the socket capture mechanism 136, and the augment section 108 may be adapted to provide the first connector 134. Further, according to some embodiments, the first connector 136 may be generally defined by a connector sidewall 138. Additionally, the connector sidewall 138 may have a variety of shapes and configurations. For example, according to some embodiments, the connector sidewall 138 may have a generally spherical-shaped configuration. However, in other embodiments, the connector sidewall 138 may provide the first connector 136 with other shapes or a combination of shapes. Additionally, the connector sidewall 138 may include one or more alignment surfaces 140a, 140b (FIG. 5) that have a shape different than the shape of other portions of the connector sidewall 138.

Figure 5:
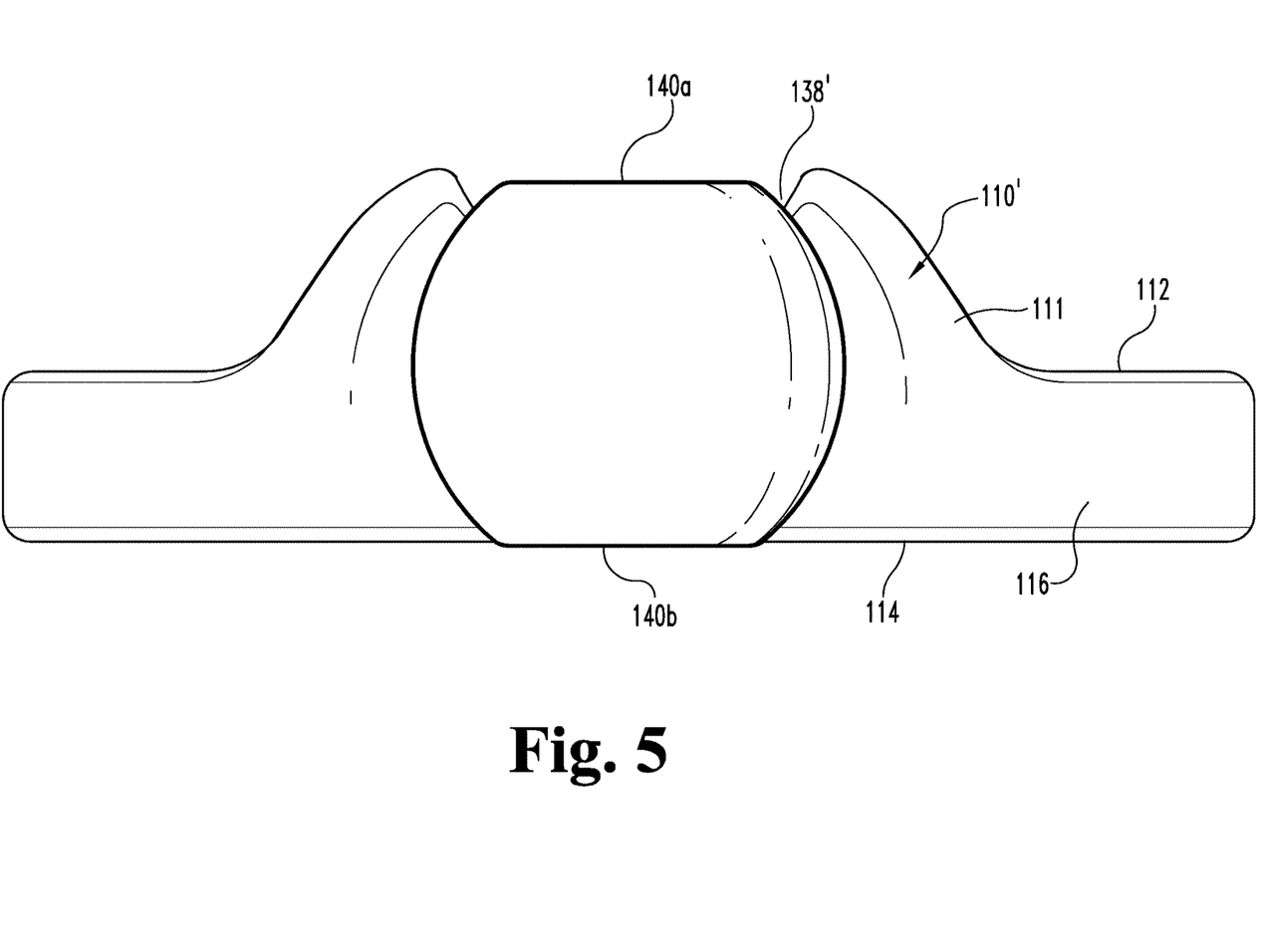
FIG. 5 illustrates a front view of the blade or plate portion of the variable angle blade augment shown in FIG. 3.

For example, in the illustrated embodiment shown in FIG. 5, while portions of the connector sidewall 138' may be generally spherical in shape, the alignment surfaces 140a, 140b may alternatively be generally flat or planar. More specifically, as shown in FIG. 5, according to some embodiments, the alignment surfaces 140a, 140b may be generally flat surfaces that are positioned on opposite sides of the connector sidewall 138', while portions of the connector sidewall 138' extending between the alignment surfaces 140a, 140b may be at least partially spherical in shape. According to other embodiments, the alignment surfaces 140a, 140b may be used in conjunction with a mating configuration of an aperture 142' of the socket capture mechanism 136' to at least indicate the general orientation of the plate or blade portion 110, 110' and augment section 108, 108' such as for example, the orientation of the augment section 108, 108' relative to the first and second sides 112, 114 of the plate or blade portion 110, 110'. Moreover, such alignment surfaces 140a, 140b, as well as a mating configuration in the aperture 142 of the socket capture mechanism 136, if any, may at least assist in providing a keyway type feature that allows for intraoperative assembly of various sized or configured plate or blade portions 110 with various other augment sections 108, 108', thereby further facilitating the modularity of the variable angle blade augment 102, 102'.

Figure 6:
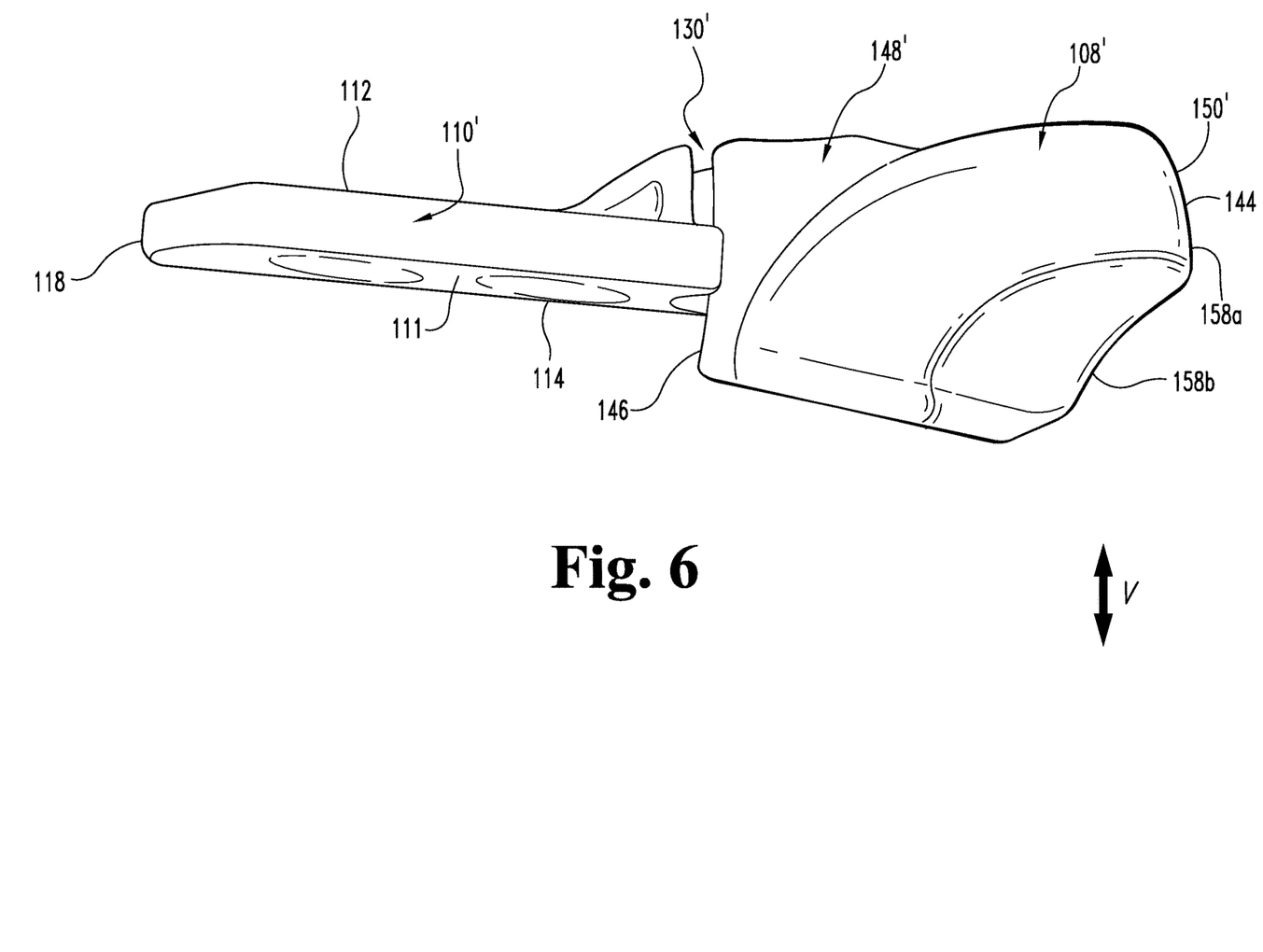
FIG. 6 illustrates a side view of the implantable medical device shown in FIG. 3, with a first connector of the plate or blade portion captured in a first end portion of an aperture of a socket capture mechanism of the augment section.

As shown in at least FIGS. 1 and 2, the augment section 108, 108' may include front and rear portions 144, 146 that are positioned on opposite sides of a body region 148 of the augment section 108, 108'. The front portion 144 may include a contoured abutment surface 150 that is shaped for abutment of at least a portion of the abutment surface 150 against at least an outer surface 152 of the acetabular cup 106. The abutment surface 150 may have a variety of different configurations including, for example, having one or more different shapes, sizes and/or segments. For example, as shown in FIGS. 1 and 2, the abutment surface 150 includes a generally curve-shaped or arcuate surface that generally extends from a first side wall 154 to a second side wall 156 of the body region 148. According to such an embodiment, the curved shape of the abutment surface 150 may generally mimic the shape of at least a portion of the outer surface 152 of the acetabular cup 106. Further, according to other embodiments, the abutment surface 150 may have a variety of different sections of the shapes and/or contours. Additionally, according to further embodiments, the abutment surface 150 may be positioned about only certain portions or segments 158a, 158b of the front portion 144 (FIG. 6). Additionally, according to still other embodiments, the abutment surface 150 may protrude or otherwise extend away from the front portion 144 and/or the body region 148.

In addition to use with modular augments, in some embodiments, the variable angle blade augment 102 may also be used with augments that have variable configurations. For example, referencing FIG. 8, in some embodiments, the variable angle blade augment 102 may be utilized with augments 108" that are designed for use on the right side of a patient (i.e., a right hand configuration), or with augments 108" that are designed for use on the left side of the patient (i.e., a left hand configuration). The manner in which the augment 108" is adapted for use on different sides of a patient may vary. According to some embodiments, the extent to which the first and second sidewalls 154, 156 extend from a location on the augment 108" for an augment 108" used in association with a right side of a patient may differ from that of augments 108" used in association with the left side of a patient. For example, according to some embodiments, the first sidewall 154 may be outwardly positioned or offset a distance away from the aperture 142" when the augment section 108" is designed for use in association with the right side of the patient's hip, and which is greater than the distance at which the first sidewall 154 is positioned away from the aperture 142" when the augment section 108" is designed for use in association with the left side of the patient's hip. Conversely, according to some embodiments, the second sidewall 156 may be outwardly positioned or offset a distance away from the aperture 142" when the augment section 108" is designed for use in association with the right side of the patient's hip, and which is less than the distance at which the second sidewall 156 is positioned away from the aperture aperture 142" when the augment section 108" is designed for use in association with the left side of the patient's hip.

Figure 7:
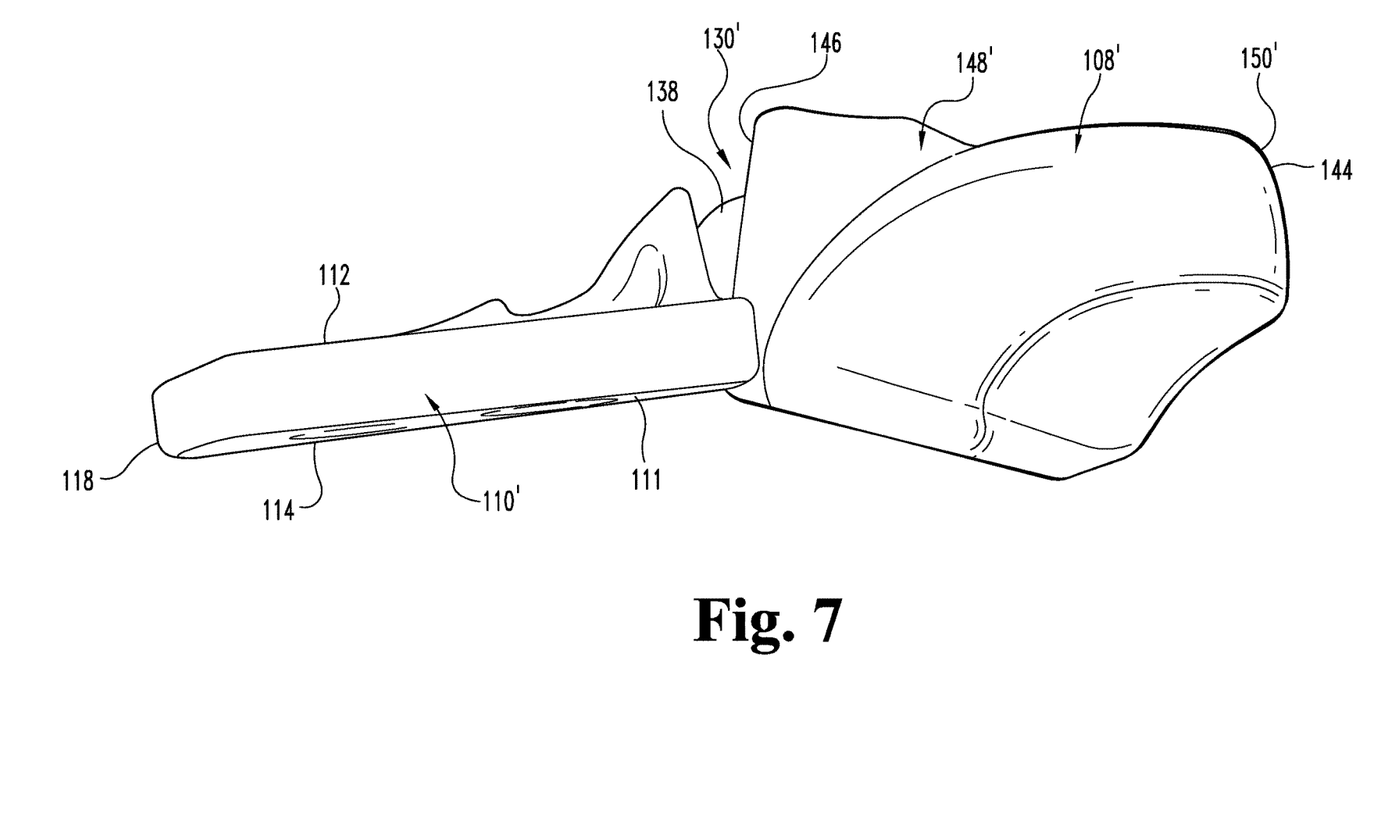
FIG. 7 illustrates a side view of the implantable medical device shown in FIG. 3 with a ball of the plate or blade portion captured in a second end portion of an aperture of a socket capture mechanism of the augment section.

As shown in FIGS. 6 and 7, according to some embodiments, the shape or profile of the abutment surface 150' of the augment section 108' may change at least along a generally vertical direction (as indicated by the "V" direction in FIG. 6). Such variations in the shape of the abutment surface 150' may provide the abutment surface 150' with one or more abutment portions 158a, 158b having different configurations that are shaped to accommodate the different angles, positions and/or orientations at which the abutment surface 150' may engage, and eventually be operably secured to, the outer surface 152 of the acetabular cup 106 via manipulation of the modified socket joint 130 during implantation of the medical device 100. For example, the abutment surface 150' shown in FIGS. 6 and 7 includes at least an upper abutment portion 158a and a differently shaped lower abutment portion 158b. Moreover, in the exemplary embodiment shown in FIGS. 6 and 7, the upper abutment portion 158a may have a generally convex shape or contour, while the lower abutment portion 158b may have a generally concave shape or contour.

Referring once again to FIGS. 1 and 2, in some embodiments the socket capture mechanism 136 may be positioned about or in proximity to the rear portion 146 of the augment section 108. For example, the socket capture mechanism 136 may include a socket wall 160 that generally extends along, away from and/or into the rear portion 146 of the augment section 108. Further, the socket wall 160 may generally define the aperture 142 that is configured to at least receive the operable placement of at least a portion of the at least semi-spherical shaped first connector 134 of the plate or blade portion 110 of the variable angle blade augment 102.

Figure 3:
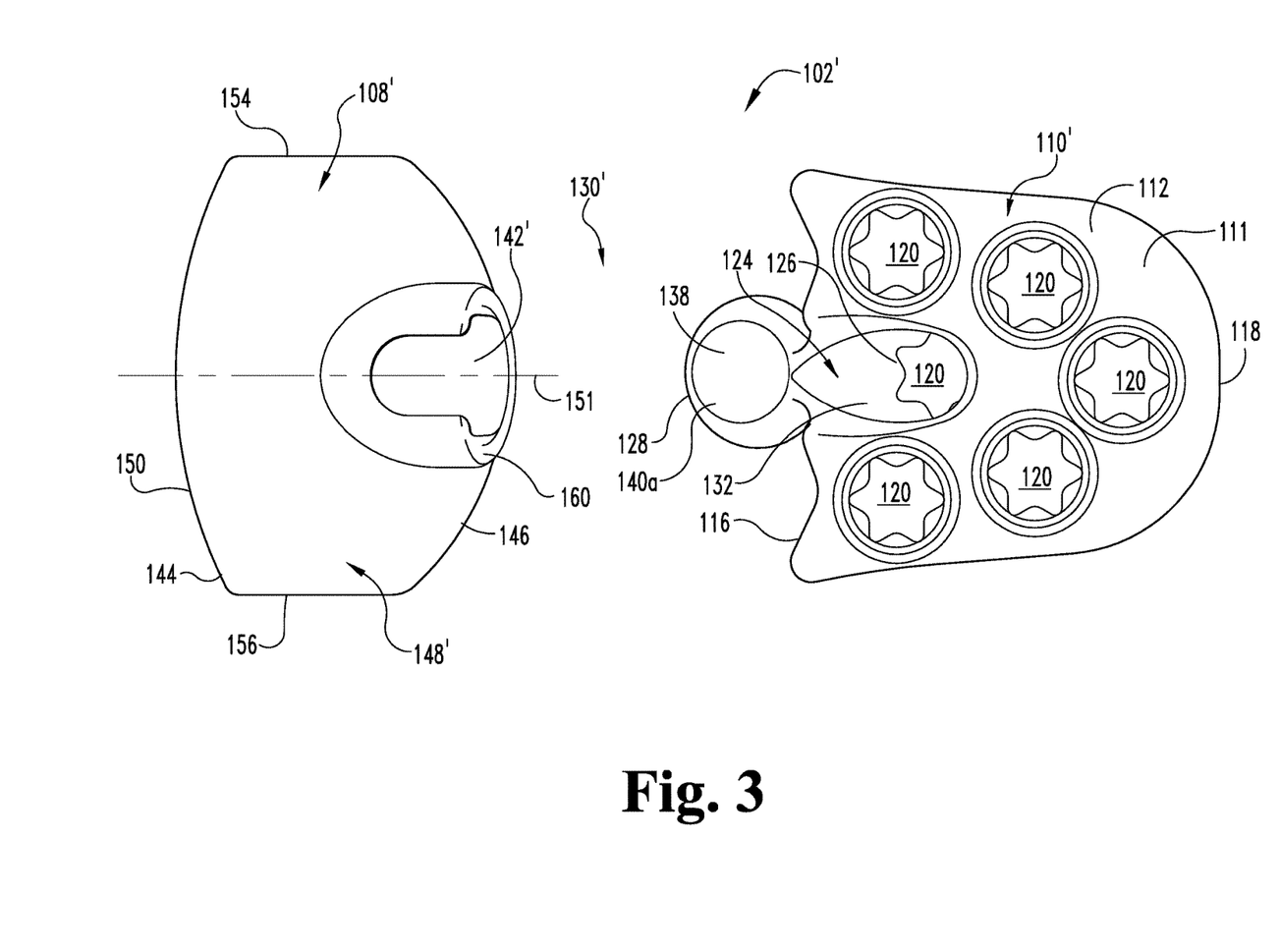
FIG. 3 illustrates an exploded top perspective view of a variable angle blade augment according to one embodiment.
Figure 4:
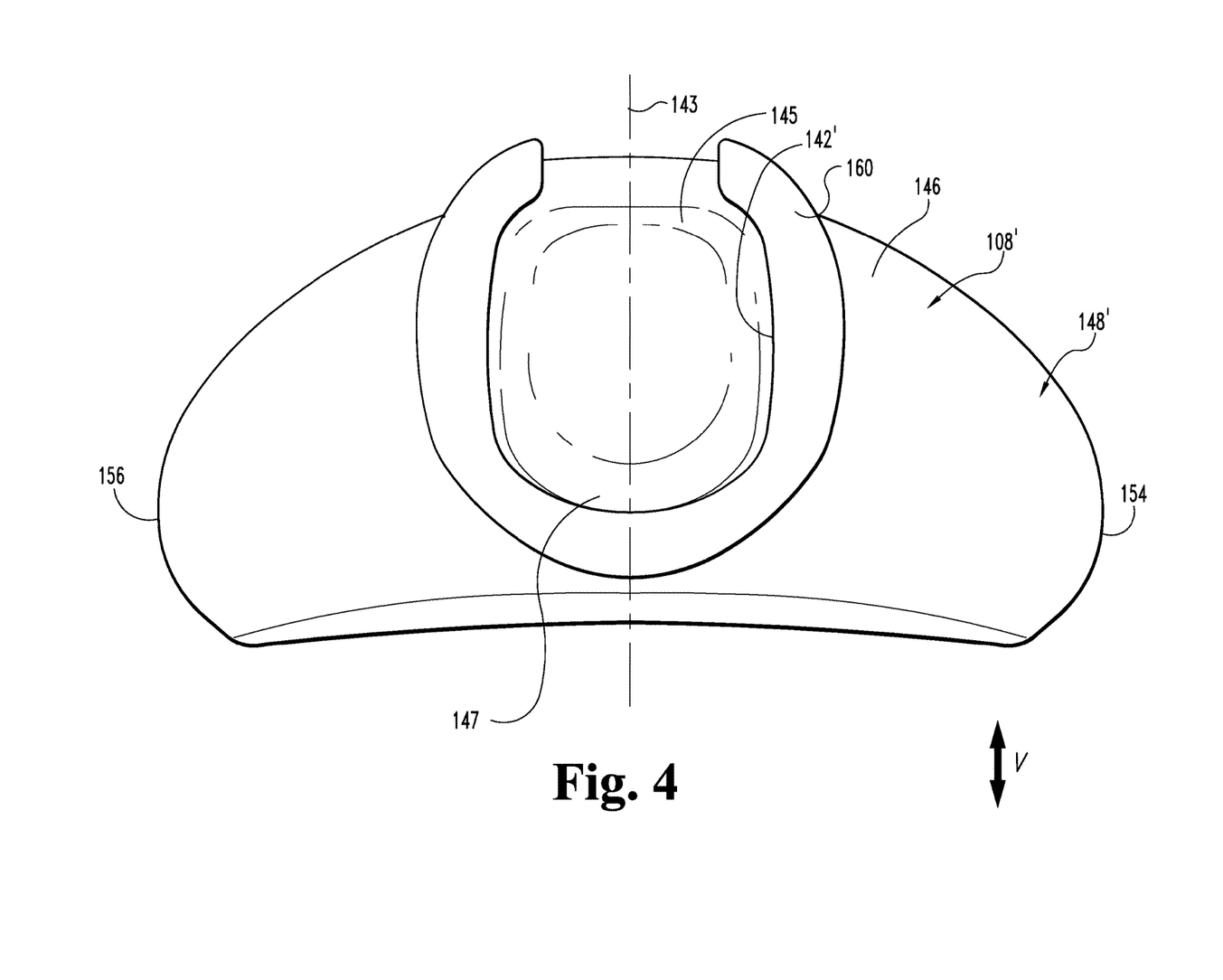
FIG. 4 illustrates a front view of the augment section of the variable angle blade augment shown in FIG. 3.

Referring to FIG. 4, according to some embodiments, the aperture 142' may be generally elongated along at least one axis. For example, as shown in FIGS. 3 and 4, the aperture 142' may be elongated along an aperture axis 143 that is arranged generally perpendicular to a central longitudinal axis 151 of a body region 148 of the augment section 108'. However, the aperture axis 143 may be positioned at a variety of other locations relative to the central longitudinal axis 151 of the augment section. Such an elongated configuration of the aperture 142' may allow for an additional range or degree of movement beyond that which may otherwise be attainable via use of a conventional ball and socket joint. For example, in addition to the relative orientation of the plate or blade portion, the augment section 108' may be pivotally adjustable via the socket joint 130', and more specifically the relative movement of the first connector 134' and/or the socket capture mechanism.

As shown in FIGS. 4 and 6, the first connector 134' may be displaced vertically (as indicated by the "V" direction) along the aperture axis 143 to a first position at a first end portion 144 of the aperture 142. Conversely, as shown in FIG. 7, the first connector 134' may also be linearly displaced along the aperture axis 143 to a second position at a second end portion 147 of the aperture 142', with the second end portion 147 being located at an end of aperture 142 that is opposite the end of the aperture 142' at which the first end portion 145 is located. Although the above examples describe the first connector 134' being positioned at opposite ends of the aperture 142', according to other embodiments, the first connector 134' may be positioned at locations between the first and second end portions 145, 147. Further, as previously discussed, in addition to being displaced along the aperture axis 143, the first connector 134' and/or the socket capture mechanism 136' may also be utilized as a ball and socket joint, thereby providing additional ranges of motion, and further facilitating the ability of the variable angle blade augment 102, 102' to accommodate a wide range of various patients' anatomies. Accordingly, the socket joint 130, 130' allows the plate, or blade portion 110, 110' to be positioned relative to the augment section 108, 108' at a greater variety of positions relative to a typically ball and socket joint arrangement, while still retaining the benefits and advantages of a ball and socket joint.

According to some embodiments, the socket joint 130, 130' may have a generally uniform configuration so as to allow the variable angle blade augment 102, 102' to provide at least a degree of modularity. For example, according to some embodiments, the blade or plate portion 110 may be offered in a variety of different sizes and/or configurations including, for example, the option or selecting from blade or plate portions 110 that have different sized or shaped body segments 111 and/or extensions 124 that extend from the body segment 111 at a variety of different distances and/or angles. Similarly, the augment section 108, 108' may also be offered in a variety of sizes, shapes, or configuration including, for example, augment sections 108, 108' that have different sized or shaped front portions 144 and/or body regions 148, as well as augment sections 108, 108' in which the socket capture mechanism 136 is located at different positions relative to the body segment 111, among other variations. According to such embodiments, one or more of the different plate or blade portions 110 may include either a first connector 134, 134' or socket capture mechanism 136, 136' that is adapted to operably engage the other of the first connector 134, 134' or socket capture mechanism 136, 136' of a plurality of different sized or configured augment sections 108, 108' so as to provide modularity that allows for the use of a variety of different sized or configured plate or blade portions 110 and augment sections 108, 108'. Such modularity may further enhance the ability to adapt the variable angle blade augment 102, 102' to a patient's anatomy of bone structure. Additionally, according to other embodiments, the plate or blade portion 110 and the augment section 108, 108' may be rapid manufactured together, thereby allowing the entire construct to be fabricated at the same time, which in turn may eliminate the need to join the plate or blade portion 110 and the augment section 108, 108' together during manufacturing or surgery.

The plate or blade portion 110 and/or augment section 108, 108' may include one or more cement ports 162 that are configured to facilitate the injection or placement of an adhesive (i.e., uncured bone cement) into at least the aperture 142, 142' of the socket capture mechanism 136. For example, according to one embodiment, the socket wall 160, 160' may include or more cement ports 162 that are in fluid communication with the aperture 142, 142' of the socket capture mechanism 136, 136'. Additionally, according to other embodiments, one or more of the cement ports 162 may be sized to receive at least a portion of an instrument or device that is used to inject the adhesive into the socket capture mechanism 136, 136' and/or about at least a portion of the first connector 136. Moreover, the one or more cement ports 162 may be configured to facilitate the flow of the adhesive between at least the connector sidewall 138 and the adjacent surfaces of the aperture 142, 142 of the socket capture mechanism 136, 136'. According to other embodiments, the first connector 134 may be configured to provide one or more troughs or pockets 168 that may further facilitate the flow of adhesive between the socket capture mechanism 136 and the first connector 134. Such adhesive (which may include, for example, relatively low viscosity bone cement or other types of adhesives) may, when cured, be used to at least assist in unitizing the plate or blade portion 110, 110' and the augment section 108, 108' at a desired orientation.

Additionally, according to some embodiments, the augment section 108, 108' may also include a reservoir positioned adjacent to and in fluid communication with at least the aperture 142 of the socket capture mechanism 136. For example, according to the embodiments illustrated in FIG. 8, one or more cement ports 160a may be positioned about an edge 164 of the body region 146 of the augment section 108, 108', 108" that provides at least a passageway for the adhesive to be delivered to the reservoir 166. Further, according to some embodiments, the cement ports 160a may be configured as directional ports that direct the flow of adhesive to the reservoir 166. Adhesive supplied to the reservoir 166 may, when cured, at least assist in securing the augment section 108, 108', 108" and in turn the variable angle blade augment 102, 102', to the acetabular cup. Additionally, according to other embodiments, in addition to, or in lieu of, use of an adhesive, the augment section 108, 108', 108" and the variable angle blade augment 102, 102' may be unitized together, or to be secured to the acetabular cup via a mechanical fastener, such as, for example, a mechanically tightened ball and socket joint. Further, such mechanical unitization can be, according to some embodiments, attained through the use of a bone screw, among other mechanical fasteners.

According to further embodiments, during at least some uses or applications, the optimal position of the plate or blade portion 110 and the augment section 108, 108' may be determined by adjusting both a linear position of the first connector 134 relative to the aperture axis 143 of the aperture 142, as well as adjusting the angular and/or pivotal orientation of the plate or blade portion 110 and the augment section 108, 108' via adjustment of the ball and socket connection provided by the socket joint 130. With the abutment surface 150 at the selected or optimal position or orientation against the acetabular cup 106, the plate or blade portion 110, 110' may be secured to the bone structure 104 via insertion of the fasteners 122 in the orifices 120, and associated engagement of the fasteners 122 with the bone structure 104. The adhesive may then be injected into at least the aperture 142 via the one or more cement ports 162 such that adhesive is positioned between the first connector 134, 134 and the socket capture mechanism 136, 136' in a manner that, when the adhesive cures, assists in unitizing the plate or blade portion 110, 110' with the augment section 108, 108'. Additionally, adhesive may also be injected via one or more cement ports 162a into the reservoir 166 so as to facilitate, when the adhesive cures, the unitization of the variable angle blade augment 102, 102' with the acetabular cup 106. Further, uncured adhesive may also be applied to the areas between the first end portion 116 of the plate or blade portion 110 and the augment section 108, 108' and/or the acetabular cup 106 to further unitize the plate or blade portion 110 with the augment section 108, 108' and/or the variable angle blade augment 102, 102' with the acetabular cup 106. According to some embodiments, the augment section 108, 108' may also include a cement buttress section that extends adjacent and above the capture socket mechanism 136, 136' and which may also be used with the adhesive to assist in unitizing the plate or blade portion 110, 110' with the augment section 108, 108' and/or the variable angle blade augment 102, 102' with the acetabular cup 106. For example, according to certain embodiments, a cement buttress section at the first end portion 116 of the plate or blade portion 110, 110' extends adjacent and above the capture socket mechanism 136, 136', and a buttress augment section 108, 108' at the front portion 144 of the augment section 108, 108' that extends adjacent and above the capture socket mechanism 136, 136' may support adhesive, such as, for example, cement, during anatomical loading of the implantable medical device 100.

Figure 8:
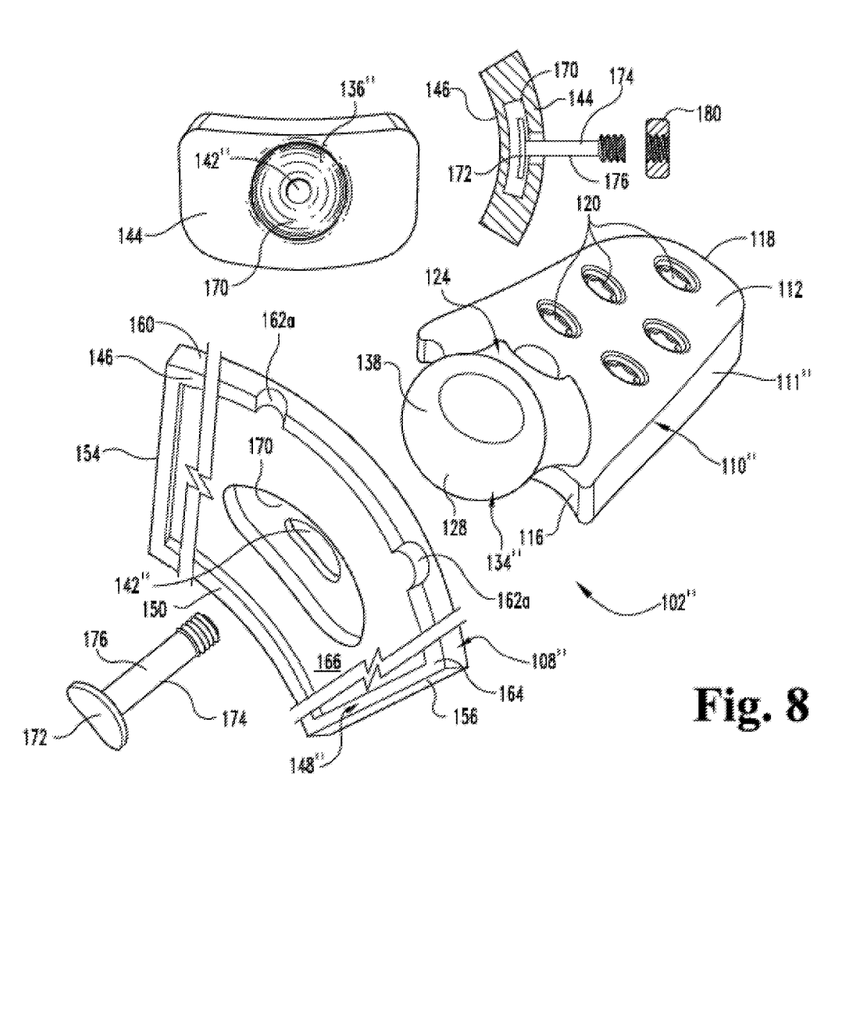
FIG. 8 illustrates an exploded perspective view of an augment section and a separate plate or blade portion according to another embodiment of a blade augment.

FIG. 8 illustrates an exploded perspective view of an augment section 108" and a separate plate or blade portion 110" according to one embodiment of a blade augment 102". In the embodiment shown in FIG. 8, a mechanical connection such as, for example, a threaded collar or nut/bolt connection or a tapered connection, may be utilized in conjunction with or in addition to an adhesive to secure the first connector 134' to the socket capture mechanism 136". Alternatively, according to another embodiment, a mechanical fastener or adhesive need not be directly used to connect the first connector 110" to the augment section 108", thereby providing non-captured socket joint 130. In other embodiments, the reservoir 166 may include a recess 170 that is adapted to securely receive a portion of a mechanical fastener 174 such as, for example, the head 172 of a lag bolt or bone screw. Moreover, the recess 170 may be sized to allow at least a body portion 176 of the fastener 174, including a threaded portion, to pass through the recess 170 and the aperture 142" while preventing passage of the head 172. The recess 170 may have variety of shapes including, for example, a generally spherical shape.

Additionally, as shown in FIG. 8, the first connector 134" may include an orifice 178 sized to receive the placement of at least a portion of the body portion 176 of the fastener 174, while also allowing a nut 180 to operably engage the thread of the fastener 174. Such a connection between the fastener 174 and the nut 180 may allow for operable securing or locking of the position and/or orientation of the augment section 108" relative to the plate or blade portion 110". According to some embodiments, the first connector 110" may continue to have at least a generally spherical shape, and optionally may be provided with alignment surfaces 140. Moreover, the first connector 110" may be structured for pivotal displacement within an aperture 142" of the augment section 108" prior to be secured in position via a mechanical fastener, such as, for example, via use of a threaded collar that mates with a portion of the first connector 110" or a bolt that extends from or through, or is otherwise operably coupled to, the first connector 110". Additionally, an adhesive may be used to at least assist in unitizing the variable angle blade augment 102" with the acetabular cup 106 including, for example, via the placement of adhesive at least in the reservoir 166 of the augment section 108" and in the gap between the first end 116 of the plate or blade portion 110" and the augment section 108" and/or the acetabular cup 106.

Various features and advantages of the present invention are set forth in the following claims. Additionally, changes and modifications to the described embodiments described herein will be apparent to those skilled in the art, and such changes and modifications can be made without departing from the spirit and scope of the present invention and without diminishing its intended advantages. While the present invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

While the invention has been described with reference to certain embodiments, it should be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A variable angle blade augment, comprising:
   an augment section including a socket wall and an abutment surface, the socket wall generally defining an aperture structured to provide a socket capture mechanism, the abutment surface structured to abut against at least an outer surface of a component of an implantable medical device; and
   a blade segment having a body segment and an extension, the body segment having a first side, a second side, a first end, and a second end, the extension having a first connector structured for at least pivotal displacement relative to the aperture, the aperture further structured to permit linear displacement of the first connector relative to opposing first and second end portions of the aperture, and wherein the body segment includes a plurality of bone fasteners extending therefrom adapted to secure the body segment to a bone structure of a patient.

2. The variable angle blade augment of claim 1, wherein the aperture has a generally elongated configuration.

3. The variable angle blade augment of claim 1, wherein the augment section includes at least one cement port that is in fluid communication with the aperture, the cement port being adapted to at least assist in the delivery or injection of an adhesive into the aperture.

4. The variable angle blade augment of claim 3, wherein the at least one cement port is positioned within the socket wall.

5. The variable angle blade augment of claim 1, wherein the socket wall extends from a rear portion of a body segment of the augment section.

6. The variable angle blade augment of claim 1, wherein the first connector includes at least one pocket structured to receive an injected adhesive.

7. The variable angle blade augment of claim 1, wherein at least a portion of the first connector is generally spherically shaped.

8. The variable angle blade augment of claim 7, wherein the first connector includes one or more alignment surfaces.

9. The variable angle blade augment of claim 8, wherein the one or more alignment surfaces comprises two generally flat surfaces positioned on opposite sides of a connector sidewall of the first connector.

10. The variable angle blade augment of claim 1, wherein the first end of the body segment of the blade segment defines a buttress surface.

11. The variable angle blade augment of claim 1, wherein the first side of the body segment is a polished surface.

12. The variable angle blade augment of claim 1, wherein the body segment includes a plurality of orifices that are each adapted to receive the insertion of one of the plurality of fasteners to secure the body segment to a bone structure of a patient.

13. A variable angle blade augment, comprising:
an augment section including a socket wall and an abutment surface, the socket wall generally defining an aperture structured to provide a socket capture mechanism, the abutment surface structured to abut against at least an outer surface of a component of an implantable medical device; and
a blade segment having a body segment and an extension, the body segment having a first side, a second side, a first end, and a second end, the extension having a first connector structured for at least pivotal displacement relative to the aperture, the aperture further structured to permit linear displacement of the first connector relative to opposing first and second end portions of the aperture; and
wherein the augment section has a body region that includes a reservoir, the reservoir being in fluid communication with at least one cement port, the reservoir structured to receive an injected adhesive that is used to unitize the variable angle blade augment with the component of the implantable medical device.

14. A variable angle blade augment, comprising:
an augment section including a socket wall and an abutment surface, the socket wall generally defining an aperture structured to provide a socket capture mechanism, the abutment surface structured to abut against at least an outer surface of a component of an implantable medical device; and
a blade segment having a body segment and an extension, the body segment having a first side, a second side, a first end, and a second end, the extension having a first connector structured for at least pivotal displacement relative to the aperture, the aperture further structured to permit linear displacement of the first connector relative to opposing first and second end portions of the aperture; and
wherein the component of the implantable medical device is an acetabular cup.

15. A variable angle blade augment, comprising:
an augment section including a socket wall and an abutment surface, the socket wall generally defining an aperture structured to provide a socket capture mechanism, the abutment surface structured to abut against at least an outer surface of a component of an implantable medical device; and
a blade segment having a body segment and an extension, the body segment having a first side, a second side, a first end, and a second end, the extension having a first connector structured for at least pivotal displacement relative to the aperture, the aperture further structured to permit linear displacement of the first connector relative to opposing first and second end portions of the aperture; and
wherein the abutment surface of the augment section has a plurality of contoured sections.

16. A variable angle blade augment, comprising:
an augment section including a socket wall and an abutment surface, the socket wall generally defining an aperture structured to provide a socket capture mechanism, the abutment surface structured to abut against at least an outer surface of a component of an implantable medical device; and
a blade segment having a body segment and an extension, the body segment having a first side, a second side, a first end, and a second end, the extension having a first connector structured for at least pivotal displacement relative to the aperture, the aperture further structured to permit linear displacement of the first connector relative to opposing first and second end portions of the aperture; and
wherein the second side of the body segment is contoured to match the anatomy of a bone structure of a patient.

17. A variable angle blade augment, comprising:
an augment section including a body region having a front portion, a rear portion, a reservoir, and an aperture, at least a portion of the front portion structured to abut against at least an outer surface of a component of an implantable medical device, the reservoir positioned in fluid communication with the aperture, the reservoir structured to receive the injection of an adhesive that is configured to unitize at least the augment section with the component of the implantable medical device; and
a blade segment including a body segment and an extension, the body segment having a first side, a second side, a first end, and a second end, the extension having a first connector adapted for pivotal displacement about an aperture of the augment section, wherein at least a portion of the first connector is structured to be secured to the augment section by a mechanical connection.

18. The variable angle blade augment of claim 17, wherein the mechanical connection comprises a threaded connection between a threaded element and a threaded collar, wherein the first connector includes an orifice structured to receive the insertion of at least a portion of the threaded element, and wherein the mechanical fastener is structured to be extended from the aperture of the augment section.

19. The variable angle blade augment of claim 17, wherein the mechanical connection comprises a tapered connection.

20. The variable angle blade augment of claim 17, wherein the body segment includes at least one cement port that is in fluid communication with the reservoir, the at least one cement port structured to facilitate the injection of adhesive into the reservoir.

\* \* \* \* \*